United States Patent
Bi et al.

(10) Patent No.: US 7,280,683 B2
(45) Date of Patent: Oct. 9, 2007

(54) METHOD, CODE, AND SYSTEM FOR ASSAYING JOINT DEFORMITY

(75) Inventors: Xiaoli Bi, Cerritos, CA (US); Joon Shim, Fremont, CA (US)

(73) Assignee: Compumed, Inc., Los Angeles, CA (US)

( * ) Notice: Subject to any disclaimer, the term of this patent is extended or adjusted under 35 U.S.C. 154(b) by 884 days.

(21) Appl. No.: 10/625,444

(22) Filed: Jul. 22, 2003

(65) Prior Publication Data

US 2004/0234116 A1 Nov. 25, 2004

Related U.S. Application Data

(60) Provisional application No. 60/397,943, filed on Jul. 22, 2002.

(51) Int. Cl.
*G06K 9/00* (2006.01)

(52) U.S. Cl. .......................... 382/132; 378/21; 378/54; 378/64; 382/131; 382/199; 382/259; 600/407

(58) Field of Classification Search ................ 128/925; 378/38, 56, 62, 21, 54, 64; 382/130, 131, 382/132, 199, 259; 600/410, 415, 416, 590, 600/407
See application file for complete search history.

(56) References Cited

U.S. PATENT DOCUMENTS

| | | | | |
|---|---|---|---|---|
| 5,413,116 A | * | 5/1995 | Radke et al. | 600/590 |
| 5,602,935 A | * | 2/1997 | Yoshida et al. | 382/132 |
| 5,671,353 A | | 9/1997 | Tian et al. | |
| 5,673,298 A | | 9/1997 | Mazess | |
| 6,002,959 A | * | 12/1999 | Steiger et al. | 600/425 |
| 6,217,214 B1 | * | 4/2001 | Cabral et al. | 378/196 |
| 6,245,109 B1 | * | 6/2001 | Mendes et al. | 623/18.11 |
| 6,246,745 B1 | | 6/2001 | Bi et al. | |
| 6,314,198 B1 | | 11/2001 | Ogura | |

(Continued)

OTHER PUBLICATIONS

Browne, M.A. et al., "Radiographic image analysis in the study of bone morphology," Clin. Phys. Physiol. Meas., 1987, vol. 8, pp. 105-121.

(Continued)

*Primary Examiner*—Gregory M Desire
(74) *Attorney, Agent, or Firm*—Perkins Coie LLP

(57) ABSTRACT

A method, machine-readable storage medium embodying computer-readable code and automated system for assaying or monitoring the extent of joint or bone deformity reported by a summarized score that may include joint space narrowing, bone erosion and periarticular osteoporosis in a joint-degenerative or joint-damaging disease in a subject are disclosed. From a digitized image of one of the subject's straight bone terminated with a joint such as fingers, coordinates of right and left bone contours of a selected middle or proximal phalange are determined, and these coordinates are in turn used to determine the coordinates of a minimum width in the middle region of the phalange and one or more apices in a region adjacent at least one side of a joint of the selected phalange. These latter coordinates are used in selecting a reference joint contour representing normal-bone contour for that phalange, or the contour of the patient phalange from an earlier x-ray image. Guided by the reference joint contour, a region of the selected joint of the patient is analyzed to assay or monitor the extent of joint or bone deformity in the subject.

27 Claims, 15 Drawing Sheets

U.S. PATENT DOCUMENTS

| | | | |
|---|---|---|---|
| 6,558,421 B1* | 5/2003 | Fell et al. | 623/14.12 |
| 6,560,476 B1* | 5/2003 | Pelletier et al. | 600/410 |
| 6,625,303 B1* | 9/2003 | Young et al. | 382/132 |
| 6,687,329 B1* | 2/2004 | Hsieh et al. | 378/62 |
| 6,690,761 B2* | 2/2004 | Lang et al. | 378/56 |
| 6,701,174 B1* | 3/2004 | Krause et al. | 600/407 |
| 6,711,282 B1* | 3/2004 | Liu et al. | 382/132 |
| 6,799,066 B2* | 9/2004 | Steines et al. | 600/407 |
| 6,839,457 B1* | 1/2005 | Azuma et al. | 382/131 |
| 7,123,762 B2* | 10/2006 | Giger et al. | 382/132 |
| 7,184,814 B2* | 2/2007 | Lang et al. | 600/416 |
| 2002/0177770 A1 | 11/2002 | Lang et al. | |
| 2003/0023156 A1 | 1/2003 | Pappas et al. | |
| 2004/0234116 A1* | 11/2004 | Bi et al. | 382/132 |
| 2007/0031015 A1* | 2/2007 | Chen et al. | 382/128 |
| 2007/0081713 A1* | 4/2007 | Jerebko | 382/128 |

OTHER PUBLICATIONS

Gaydecki, P.A. et al., "Measurement of radiographic changes occurring in rheumatoid arthritis by image analysis techniques," Annals of the Rheumatic Diseases, 1987, vol. 46, pp. 296-301.

PCT International Search Report for International Application No. PCT/US03/23045, dated Nov. 14, 2003, 4 pages.

* cited by examiner

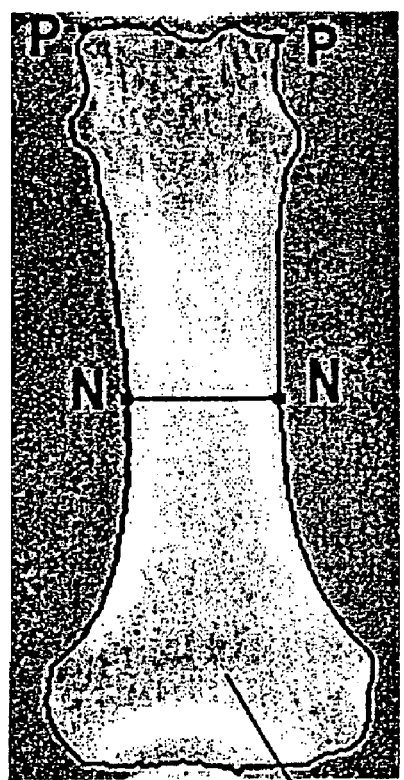 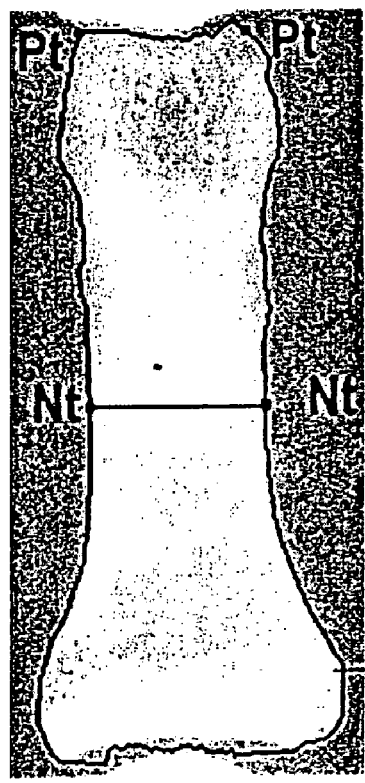
FIG. 8A
108
FIG. 8b
110

108    110

108,110

108,110

108,110

METHOD, CODE, AND SYSTEM FOR ASSAYING JOINT DEFORMITY

This application claims the benefit of U.S. Provisional application Ser. No. 60/397,943, filed Jul. 22, 2002, which is incorporated herein by reference in its entirety.

FIELD OF THE INVENTION

The present invention relates to an automated method and system for assaying or monitoring the extent or progression of joint or bone deformity in a joint-degenerative or joint-damaging disease, such as osteoarthritis or deformity joint disease such as rheumatoid arthritis.

BACKGROUND OF THE INVENTION

There are a variety of joint-degenerative and joint-damaging diseases, such as various forms of arthritis and osteoporosis, that have important health and quality-of-life consequence to patients. Since these diseases tend to be progressive, it is also important to be able to monitor change in joint or bone deformity, for example, in monitoring treatment methods.

A variety of biochemical and physical analysis tools are available for monitoring bone and joint resorption and degeneration conditions. These methods suffer various limitations relating to ability to pinpoint and accurately quantitate joint-degenerative conditions in an automated or substantially automated way.

SUMMARY OF THE INVENTION

The invention includes, in one aspect, an automated method of assaying or monitoring the extent of joint or bone deformity in a joint-degenerative or joint-damaging disease such as osteoarthritis or osteoporosis, or deformity joint disease such as rheumatoid arthritis, in a subject. The method includes first determining from a digitized image of a patient's selected straight bone that terminates at a joint, coordinates of at least one of the right and left bone contours of a selected bone, and determining from the bone contour coordinates above, one or more apices in a region adjacent at least one side of a joint of the selected bone, and, optionally, the coordinates of a minimum width in the middle region of the bone.

The coordinates so determined are used for selecting a reference bone contour corresponding to one of (i) the contours of confronting joint portions of adjacent straight bones in a normal joint formed by the selected bone; (ii) the contour of a normal joint in a joint region formed by the selected bone; and (iii) the contour from previous x-ray of the subject's bone in the region of the joint. Guided by the reference bone contour, a region of the selected bone of the patient is analyzed to assay or monitor the extent of bone deformity in the subject.

The selected bone may be a finger phalange defining a finger joint, or a toe phalange defining a toe joint. An exemplary bone is the middle or proximal phalange of a patient's finger. The step of selecting a reference bone contour may include matching contour coordinates for a selected patient phalange with one or more of a plurality of normal-phalange templates from a library of templates. The normal-phalange templates in the library may generated, for given patient characteristic(s) related to one or more of gender, age, ethnic group, hand size and body size, as a statistical average of a plurality of normal-phalange templates for the given patient characteristic(s).

In one general embodiment (Embodiment 1) for use in assaying or monitoring joint space width in a patient joint, the selecting step may include (i) matching the coordinates of a minimum width in the middle region of the phalange and one or more apices on at least one side of the selected phalange adjacent the joint with corresponding coordinates in a normal-finger template, to identify a normal-finger template that matches the subject phalange, (ii) superimposing the normal-finger template phalange on the image of the patient-finger phalange, and (iii) using the contours of the template finger to identify a scanning box at one of the joints of the selected phalange.

Selecting step (i) may include using the coordinates of the minimum phalange width to determine a scaling factor for superimposing the template finger of the image of the patient finger. This step may further include matching the determined coordinates of a patient-finger flange with the corresponding coordinates of the phalange from one or more of a set of template phalanges, assessing the difference between the two, and based on this difference, either accepting the template or matching another template from the set.

Selecting step (iii) may include finding a first line extending through the widest portion of the middle phalange in the region of the MP/PP joint, finding a second line parallel to the first which extends through the widest portion of the adjacent phalange in the region of the same joint, and connecting the two lines with parallel connecting lines to form a rectangular scanning box defined by the widest bone portions.

The analyzing step may include scanning one of the joints of the selected phalange within the scanning box, in scanning directions substantially parallel to the axis of the finger, to generate contours of the confronting ends of the phalanges in the joint, (ii) generating a profile of the distances between the confronting phalange bone-end contours within the scan box, and (iii) analyzing the profile from (ii) to determine the distance between the confronting ends of the phalanges defining the joint space width and the extent of bone loss at the joint, as an indicator of extent or progression of joint-damaging disease in the subject.

The analyzing step may further include successively scanning across the joint, in a direction substantially parallel to the finger axis, and the scan line an incremental distance along the width of the scan box, until scans along the entire width of the box have been taken.

One exemplary phalange is the middle phalange, and the scanning box is placed at the middle phalange/proximal phalange (MP/PP) joint, and scanning step (ii) includes comparing the distances at each point along the scan box in the profile with those representative of a normal-subject MP/PP joint from the same finger as the patient finger.

In an embodiment (Embodiment 2) for use in assaying or monitoring bone erosion in a patient joint, the selecting step may include (i) from the determined coordinates of the contours of the selected phalange, identifying a pair of apices on at least one side of the selected phalange adjacent the joint, and (ii) constructing a straight line between the apices in each pair, where the straight line represents a reference joint contour adjacent the joint region of the selected phalange. The analyzing step includes comparing the straight-line contour between a pair of apices with the actual patient contour between the same two points, to determine the extent of concavity of said region with respect to the straight line extending between the two apices.

In another embodiment (Embodiment 3) for use in assaying or monitoring bone erosion in a patient joint, the selecting step may include (i) matching the coordinates of a minimum width coordinate in the middle region of the phalange and one or more apices on at least one side of the selected phalange adjacent the joint with corresponding coordinates in a partial or complete normal-finger template, to identify a joint region of a normal-finger phalange template that matches the subject finger joint region, and (ii) superimposing the contour of the template phalange joint region on the image of the patient-finger phalange joint region, where the template contour represents a reference joint contour adjacent the joint region of the selected phalange. The analyzing step includes comparing the template line contour in the joint region with the actual patient contour in the same region, to determine the extent to which the actual patient contour deviates from the normal-phalange contour.

In still another embodiment (Embodiment 4) for use in assaying or monitoring bone erosion in a patient joint, the selecting step may include (i) matching the coordinates of a minimum width coordinate in the middle region of the phalange and one or more apices on at least one side of the selected phalange adjacent the joint with corresponding coordinates in a previous patient x-ray image of the finger phalange, and (ii) superimposing the contour of the previous x-ray image phalange on the image of the patient-finger phalange, where the previous-patient contour represents a reference contour of the selected phalange. The analyzing step includes comparing the previous-image contour in the joint region with the actual patient contour in the same region, to determine the extent to which the actual patient contour deviates from the previous-image contour.

In another aspect, the invention includes machine-readable storage medium embodying computer-readable code which is operable, when used to control the operation of an electronic computer, to carry out the steps in the above method for assaying or monitoring the extent of joint or bone deformity in a joint-degenerative or joint-damaging disease.

Also disclosed is an automated system for use in assaying or monitoring the extent of joint or bone deformity in a joint-degenerative or joint-damaging disease, such as arthritis or osteoporosis. The system includes an electronic computer, and machine-readable storage medium embodying computer-readable code which is operable, when used to control the operation of the computer, to carry out the steps in the above method, where the selecting step in the method includes matching contour coordinates for a selected patient phalange with one or more of a plurality of normal-phalange templates from a library of templates. The system also includes a library of normal-phalange templates that is accessible by the code for use in carrying out the selecting step in the method. The library forms yet another aspect of the invention.

These and other objects and features of the invention will become more fully apparent when the following detailed description of the invention is read in conjunction with the accompanying drawings.

BRIEF DESCRIPTION OF THE DRAWINGS

FIGS. 8A and 8B show minimum width (N) and apical points (P) in a patient phalange joint region (8A) and corresponding template joint region (8B);

FIGS. 14A-4E show steps in correcting finger axis in severely curved finger.

DETAILED DESCRIPTION OF THE INVENTION

As described above, the invention includes an automated method for monitoring or assessing the extent of joint or bone deformity in a joint-degenerative or joint-damaging disease, such as arthritis or osteoporosis or deformity joint disease such as rheumatoid arthritis, and a system and machine-readable code, for carrying out, or assisting medical personnel in carrying out the method. The code is in the form of a machine-readable storage medium embodying computer-executable code which is operable to control an electronic computer, as will be readily understood from the description of the operation of the code herein. The method will be illustrated with respect to four general embodiments:

Embodiment 1 is intended for use in measuring the joint space width (JSW) in a selected joint, e.g., the MP/PP joint between the middle phalange (MP) and the proximal phalange (PP) and/or the joint PP/MC joint between the PP and metacarpal (MC) bone in a patient's hand. In particular, the method is intended to assay or monitor damage in this joint, as evidenced, for example, by a less-than-normal JSW in the joint.

Embodiments 2-4 are each designed for assaying bone erosion in the joint region of one or both bones forming the joint, e.g., the regions adjacent the confronting joint regions of the MP or PP, or adjacent the confronting joint regions of the PP and MC. In all three embodiments, bone erosion is measured as the difference between a reference contour in the joint region of the selected bone and the actual patient contour in the same region of the bone. The reference contour in Embodiment 2 is a straight line between a pair of apical points on one or both sides of the joint region of the bone; in Embodiment 3, the reference contour corresponds to a normal-bone template, either partial or complete, that is superimposed on the patient joint region; and in Embodiment 4, the reference contour is generated from an earlier x-ray image of the same patient bone, allowing a change in bone erosion over time to be monitored.

The method is based on computer analysis of digitized x-ray images of joints in a patient's long bones, typically one or more flanges or the patient's finger of toe bones, but optionally including other long or elongate bones that terminate in a joint, such as the long bones of the arm or legs. For purposes of description, the method will be described with particular reference to images of a patient's hand, it being understood how the method would be applied to other long bones.

Figure 1:
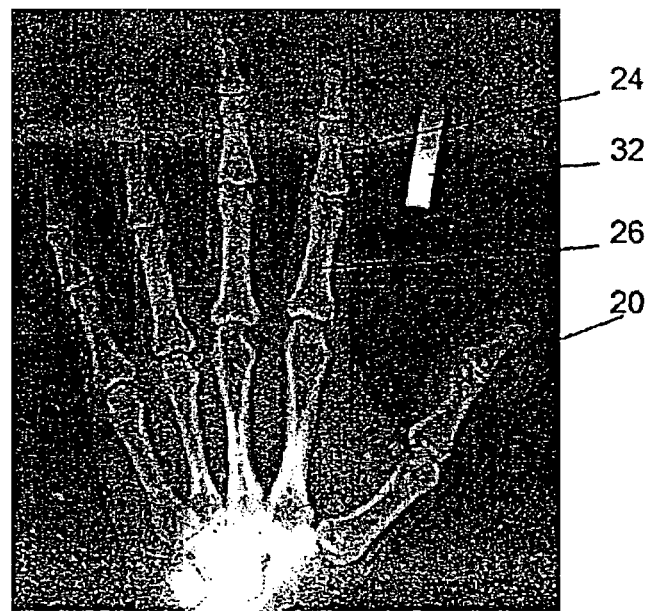
FIG. 1 shows an x-ray image of a patient hand, with a calibration wedge in the image shown at the upper right in the figure.
Figure 3:
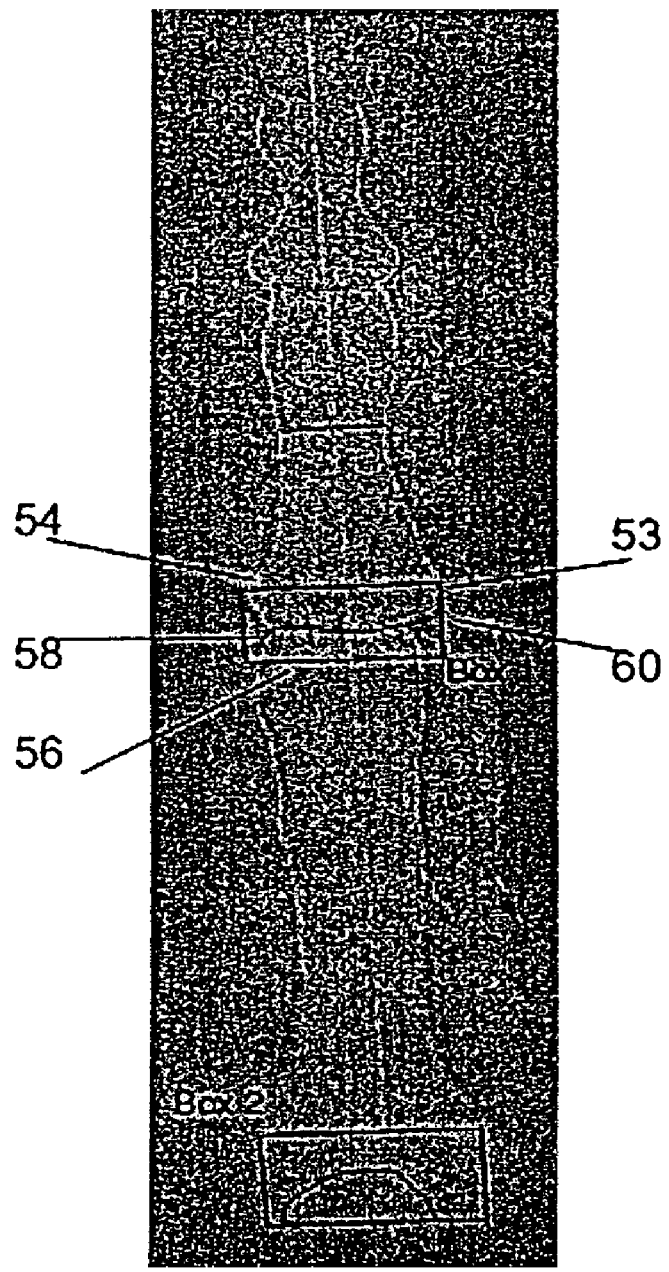
FIG. 3 is a portion of an x-ray image of a patient finger, showing scanning boxes at the MP/PP and PP/MC joints.

The x-ray or fluoroscopic image of a patient's hand may be obtained using conventional x-ray methods. At a minimum, the x-ray image should include at least one and preferably three fingers on at least one hand of the patient, where the image of each finger includes all of the middle phalange (MP), all of the proximal phalange (PP), and therefore the MP/PP joint, and enough of the metacarpal phalange or bone (MC) to provide an image of the PP/MC joint for that finger. A preferred image contains three digits of a hand and a calibration wedge, as illustrated for example in FIG. 1 and detailed with respect to FIG. 3 and in column 6, lines 37-49 of co-owned U.S. Pat. No. 6,246,745 B1 ('745 patent). The '745 patent is incorporated herein in its entirety. FIG. 1 is an x-ray image 20 of a patient's left hand, showing fingers such as index finger 22, and phalanges, such as the middle phalange (MP) 24, proximal phalange (PP) 26, and the metacarpal bone (MC) 30. Also shown in the figure is a calibration radio-opaque wedge 32.

The x-ray image is digitized, according to known methods, such as disclosed in the '745 patent, for example, at column 10, lines 21-27, yielding, for example, a 12-bit grey scale image with a resolution of at least 230 dpi. A segmentation and processing module (also forming part of the machine-readable storage medium embodying computer-readable code of the present invention), such as described in the above '745 patent, column 12, line 47 to column 13, line 23, and in related passages describing processing steps 160, 164, 168, 174, 178, and 184) then carries out the following image processing steps:

(1) The three digits, e.g., the index, second, and third fingers, and the calibration wedge are segmented from the background (processing step 160).

(2) The contour points (x,y coordinates) of the three digits and wedge are stored (processing step 164).

(3) The central axis of each of the three digits is determined and stored (processing steps 168 and 174).

(4) The left bone edge and the right bone edge of each digit are determined (processing step 178).

(5) The contour points (x,y coordinates) of the left and right bone edges are stored (processing step 184).

Once these operations have been performed, the program operates to determine the coordinates of one or more apices, i.e., points of maximum lateral extension or projection, adjacent at least one side of a joint of that phalange, e.g., at least one side region of the middle phalange MP/PP joint. The apices may be local maxima, allowing for more than one apex along each side region of a joint. Optionally, the program also determines the coordinates of the minimum width in the middle region of a selected phalange, e.g., the MP or PP. As will be seen below, both apical and minimum width coordinates are typically used in selecting reference contours, although in one embodiment (Embodiment 2), minimum-width coordinates may not be required.

The coordinates determined from above are then used in selecting reference contours that are employed in the joint or bone analysis. For Embodiment 1, the reference contours are the contours of confronting portions of adjacent phalanges in a normal-finger joint. In Embodiments 2 and 3, the reference contours selected are the contours of a normal-finger joint in a region adjacent at least one side of a joint of the selected phalange. The "normal-finger" contour may be represented either by a straight line between a pair of apical joints adjacent the joint region (Embodiment 2), or a contour from a normal-bone template in that joint region (Embodiment 3). In Embodiment 4, the reference contour is derived from an earlier patient x-ray image of the same bone region.

Guided by the reference joint contours identified as above, a region of the selected joint of the patient is then scanned to assay or monitor the extent of joint or bone degeneration in the subject.

A. EMBODIMENT 1

Measuring JWS

Figure 2A:
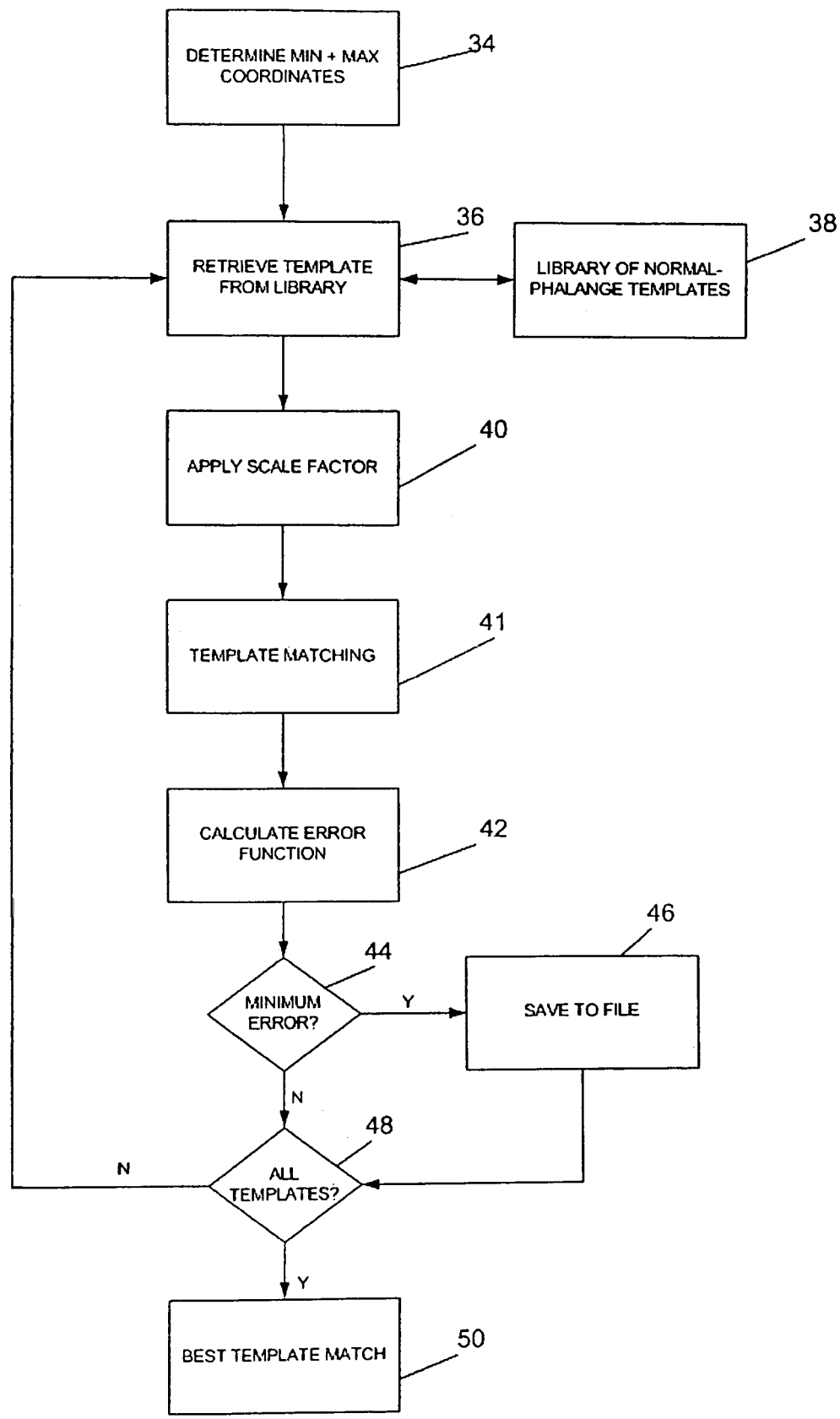
FIGS. 2A and 2B are flow diagrams of the operation of the system in carrying out Embodiment 1 of the invention.
Figure 2B:
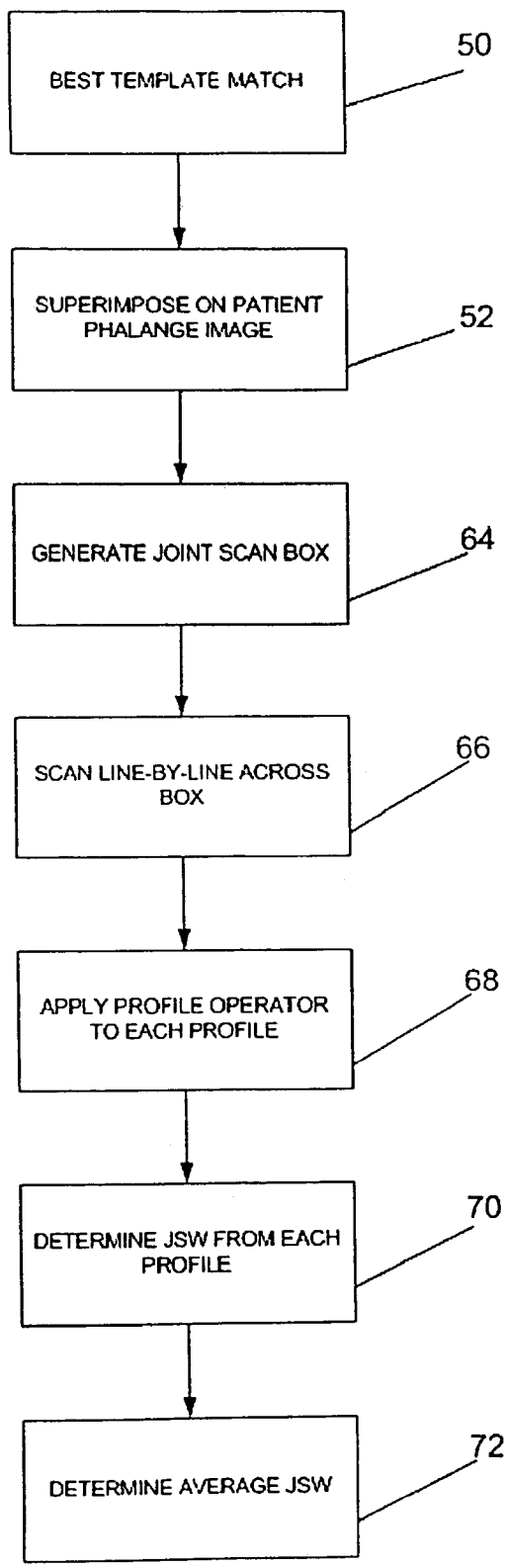

FIGS. 2A and 2B show a flow diagram of steps performed by the machine-readable storage medium embodying computer-readable code of the invention, in carrying out the method of Embodiment 1. As indicated by box 34 in the figure, the coordinates that are determined from the x-ray images are the coordinates at the left and right edges of the bone at its narrowest width (Min), and the apical coordinates corresponding to coordinates at the ends of a line through the widest portion of the phalange (Max) adjacent one or both joints of that phalange, for example, the greatest widths at the top and bottom joint regions of the middle flange.

The coordinates are determined by using the left and right bone edge contours to find the minimum bone width of the middle phalange. Starting from the first coordinate of the left bone edge contour, the program finds the corresponding coordinate that has the same Y coordinate from the right bone edge contour. The width at this Y coordinate will be the difference between the two X coordinates. After creating the width profile, the middle phalange minimum width coordinates and the coordinates at the widest points of both top and bottom joint regions are determined. Embodiment 3 below details the algorithm for finding minimum width coordinates. The same approach is used for finding coordinates at a maximum width in the joint regions of the selected phalange.

Once these coordinates are determined, the program operates at 36 to find a normal-bone template that closely matches the selected patient phalange, e.g., the MP, in size and shape. The templates are selected from a library 38 of normal-bone phalanges. Each template in library 38 is a collection of contour points of a phalange, and is defined as $T(x_i, y_i)$, i=0, 1, . . . . n, where n is the total number points of the contour.

The template may be generated statistically or arbitrarily. A statistical template can be made after sampling a large number of normal phalange data and "averaging" them. This requires a large set of "good representative" data. An arbitrary template is created using a selected phalange contour. This is possible when the shape of an object of interest is uniform and regular. The statistical template will preferably be specific for gender, height and/or hand size. In order to cover minor variations in shape of phalanges depending on gender and age group, there is a preferable set of templates for each finger's every phalange. In an exemplary method, and based on the matching time and the shape variances, five to six templates for each set are chosen.

A selected template from the set is then overlaid on a real bone image. The minimum width of the middle phalange found from above is used as an anchor point to overlay the template. A scale factor (SF) is calculated at 40 based on the size of the finger, i.e., the height and the minimum width of the patient's middle phalange. It is defined as $$SF = \frac{\max(y) \in T(x, y) - \min(y) \in T(x, y)}{\max(y) \in R(x, y) - \min(y) \in R(x, y)}$$

where T(x,y), R(x,y) represent the template and real bone respectively. With the anchor point as well as the scale factor, the template is shrunk or expanded to fit the real phalange. The scaled template is superimposed on the patient phalange for template matching, as at 41. An error parameter r (box 42) is used to evaluate the "goodness" of the match.

$$r = \sum_{i=1}^{n} |R(x_i, y_i) - T(x_i, y_i)|^2$$

All the templates in an appropriate set will participate in the matching process by repeating the matching steps as described. The logic of the template selection is shown at 44-50 in FIG. 2A. Briefly, a minimum error function r for all templates tested is stored. This lowest error function is compared with the error function of the latest template match at 44. If the latest template match is lower than the stored error function, the new match is saved to file 46 along with its error function. If the latest template error function is higher than the existing function, the program proceeds to test the next template, through the logic of 48, 49, until all of the library templates have been tested against the selected patient phalange. When this process is completed, the template having the lowest error function is identified as the best match template, at 50. That is, if the error parameter of the match between the patient-image middle phalange and the template is within a predefined range, the template is retained; otherwise, a new template is evaluated, and the process repeated until an appropriate template is found, either as a good-match or as the best-match, i.e., the one with the minimum error.

The template that generates the minimum error parameter is selected for the next stage operations, which are given in flow diagram form in FIG. 2B. Once a MP template is found, it is superimposed on the patient template, at 52, and using the outlines of the template, the program constructs a rectangular scan box 53 (Box 1, the upper box in FIG. 3) for the MP/Proximal phalange (PP) joint is defined by (a) two parallel lines 54, 56 (see also FIG. 4) extending between the widest portions of MP and PP.

(b) two parallel lines 58, 60 (see also FIG. 4) extending between the ends of the MP widest-portion line and extensions of the PP widest-portion line.

Figure 4:
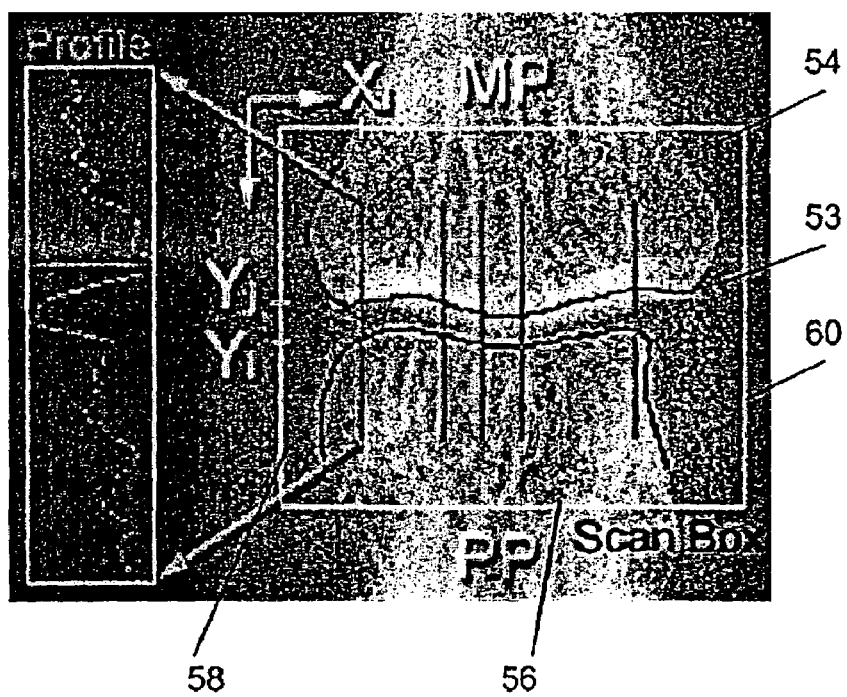
FIG. 4 is an enlarged view of the of the MP/PP joint scan box shown in FIG. 3.

The construction of the scanning box is indicated at 64 in FIG. 2B. A scanning and profile analysis algorithm given in FIG. 2B is now employed to scan the patient MP and PP bone-end contours, by scanning in a direction parallel to the bone axis, across the entire length of Box 1. Inside the scan box is a small sub-image as shown in FIG. 4 including joints between either MP and PP or joints between PP and MCP. A series of mathematical image processes including Unsharp Mask, Local Equalization and Median Filter are then be applied to the sub-image for the purpose of enhancing image quality by reducing both the high and low frequency noise.

With reference to FIG. 4, which shows scanning box 53 in enlarged view, the start point will be the center point of the scan box, indicated by scan line 62. The program scans line-by-line parallel to the bone axis (vertical in FIG. 3) toward each side of the box until reaches the two ends. This operation is indicated at 66 in FIG. 2B. A gray level profile is then created for each scanned line.

For each profile, its optical density curve is analyzed to extract JSW after a Sobel operator is applied, as shown at 68 in FIG. 2B. The concept of the Sobel operator is to find the gradient of a function f at coordinates (x,y). It is defined as:

$$\Delta f = \begin{bmatrix} \frac{\partial f}{\partial x} \\ \frac{\partial f}{\partial y} \end{bmatrix}$$

and the magnitude of this vector is $$\Delta f = mag(\Delta f) = \left[\left(\frac{\partial f}{\partial x}\right)^2 + \left(\frac{\partial f}{\partial y}\right)^2\right]^{1/2}$$

By analyzing each profile using this operator, an interface between the end of MP bone and the joint area as well as the end of PP bone and the joint area can be detected. Let $y_j$ be the y coordinate at the bottom bone outline of the upper phalange, and $y_i$ be the y coordinate at the top bone outline of the bottom phalange, marking two coordinates per profile ($R(x_i,y_i)$ and $R(x_j,y_j)$), MP and PP bone end contours will be formed from the bone/joint interface coordinates. The contours of a MP/PP joint are shown in the corresponding scan box in FIG. 4, and the operation of determining JSW for each scan profile, indicated at 70 in FIG. 2B. The joint space width $w(x_i)$ at coordinates ($x_i,y_i$) is defined as:

$$w(x_i) = abs(y^j - y^i)$$

The distances between the contours of MP/PP joint are averaged, as at 72 in FIG. 2B, to create the MP/PP joint space width, $$JSW = \sum_{i=1}^{n} w(x_i) \quad i = 1, 2, \ldots n$$

A similar approach is used to determine the joint space narrowing at the PP/MCP bone joints. Based on the top portion of the PP contour from the operation above, the MP width and height, the program calculates a scale factor for the PP. With this scale factor, a PP template (preferably taken from the same template set for the MP) is overlaid. The match process is similar to that described above for the MP. This approach assumes that the axis of the finger is a straight line. If this is not the case, the PP template has to be rotated with respect to the MP until the two template phalanges are aligned with the patient phalanges.

In particular, once the PP template is overlaid, it is possible to

1. Define a scan box (lower box in FIG. 3) from the widest portions confronting MP and MCP bones;

2. Scan the PP/MCP joint in directions parallel to the finger axis, to generate bone-end contours;
3. Generate a profile across the joint of the distance between the bone-end contours, and
4. Use this profile to assess the degree of joint loss between the PP and MCP.

This score provides another indicator of the extent or progression of joint loss in the patient hand.

B. EMBODIMENT 2

Measuring Joint Bone Erosion

Erosion happens in early stages in RA patients and it rapidly gets worse in the first few years of the disease. When a patient is first seen, the physician's objective is to detect the existence and the severity of bone erosion. At this time the contours of the interested bones are obtained for the first time and saved as baseline results for future monitoring purpose. Embodiment 2 described in this section and Embodiment 3 described in the next sections are designed to assess the extent of bone loss in the joint region of a selected bone, e.g., phalange, using normal-bone contours to as reference contours. In follow-up visits, the patient's own earlier x-ray images may be used as the reference contours, for assessing the change in bone erosion over time. This approach is detailed below as Embodiment 4.

When the patient's bone contours are obtained for the first time, there are no preexisting contours to reference in the database. Since there are wide variances in the shape of bones of interest, it may not be straightforward to use templates in order to detect erosion in this situation. To overcome this difficulty, the method of Embodiment 2 utilizes a method of determining convex—concave property of the top portion of the lateral bone contours.

Figure 6:
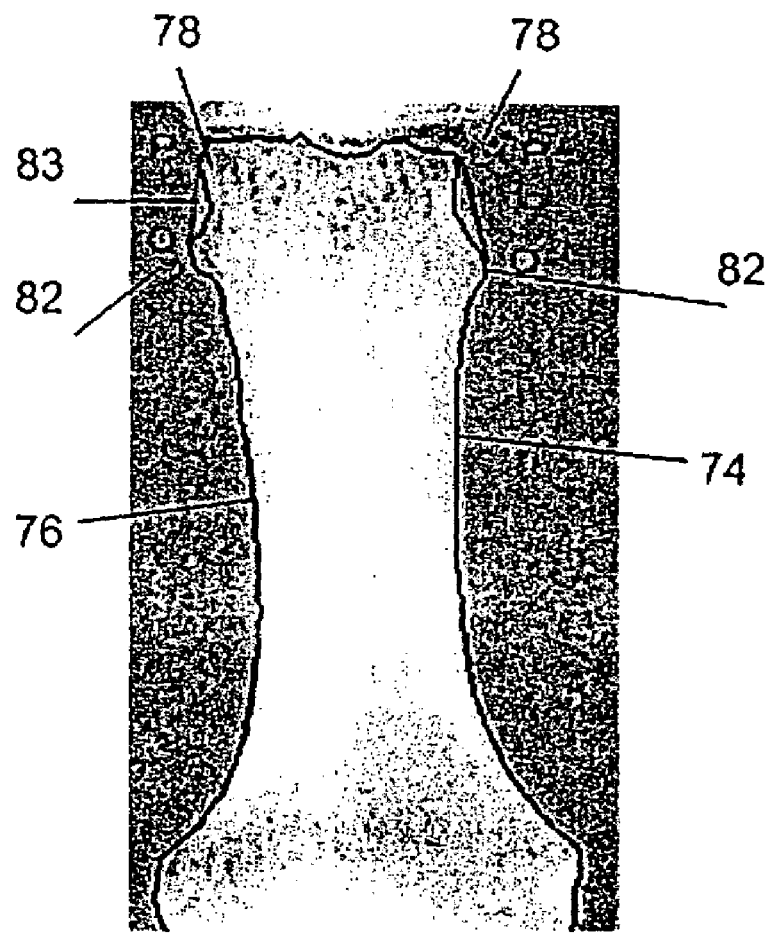
FIG. 6 illustrates apical-point reference and patient-bone contours in the distal joint region of PP.

FIG. 6 shows the concave property of a PP phalange 74 having a contour 76 shown in black trace. In an AP (anterior-posterior) fingers x-ray, with no excessive rotation of the fingers along the center axis, the normal shape of the top portion of the bones of interest exhibits an outward convex. If erosion has taken place, it is possible to detect various concave shapes in those areas. Using two points and a straight line that connects them, it is possible to determine how concave the contour is in the area and thus the existence of erosion.

To illustrate the algorithm in detail, consider only one side, e.g., the left top quarter of the bone contour in FIG. 6. In this illustration, contour 76 of the phalange has two distinctive apices (maxima), point P and point Q. Apical point P, indicated at 78, is found by the algorithm below, corresponding to box 80 in FIG. 5, which is a flow diagram of the steps in the method. By scanning the left lateral portion of the contour from its upper tip down through one quarter of its full length, the point on this segment with its $X_i$ coordinate value smaller than $X_{i+1}$ identifies point P.

$$P=(x_i,y_i) \in B_L$$

where $B_L$ is a defined portion of the left side bone contour. In this case, the algorithm uses a quarter length of the whole contour in this study, and $x_j < x_{j+1}$, where $(x_{i+1},y_{i+1}) \in B_L$, and $m \leq i \leq q$, where $(x_m,y_m) \in B_L$ and $ym=\min(y) \in B_L$ $(x_q,y_q) \in B_L$ and $$y_q = \frac{\max(y) \in B_L - \min(y) \in B_L}{4}$$

The second point, Q, shown at 82 in FIG. 6, is determined by the same method as described above but by scanning the contour in a bottom-up direction. These steps are generally represented by box 84 in FIG. 5.

$$Q=(x_j,y_j) \in B_L$$

Where $xj < x_{j+1}$ and $(x_{j+1},y_{j+1}) \in B_L$ and $yi \neq y_j$, and $q \geq j \geq m$, m and q are defined the same as above.

Figure 5:
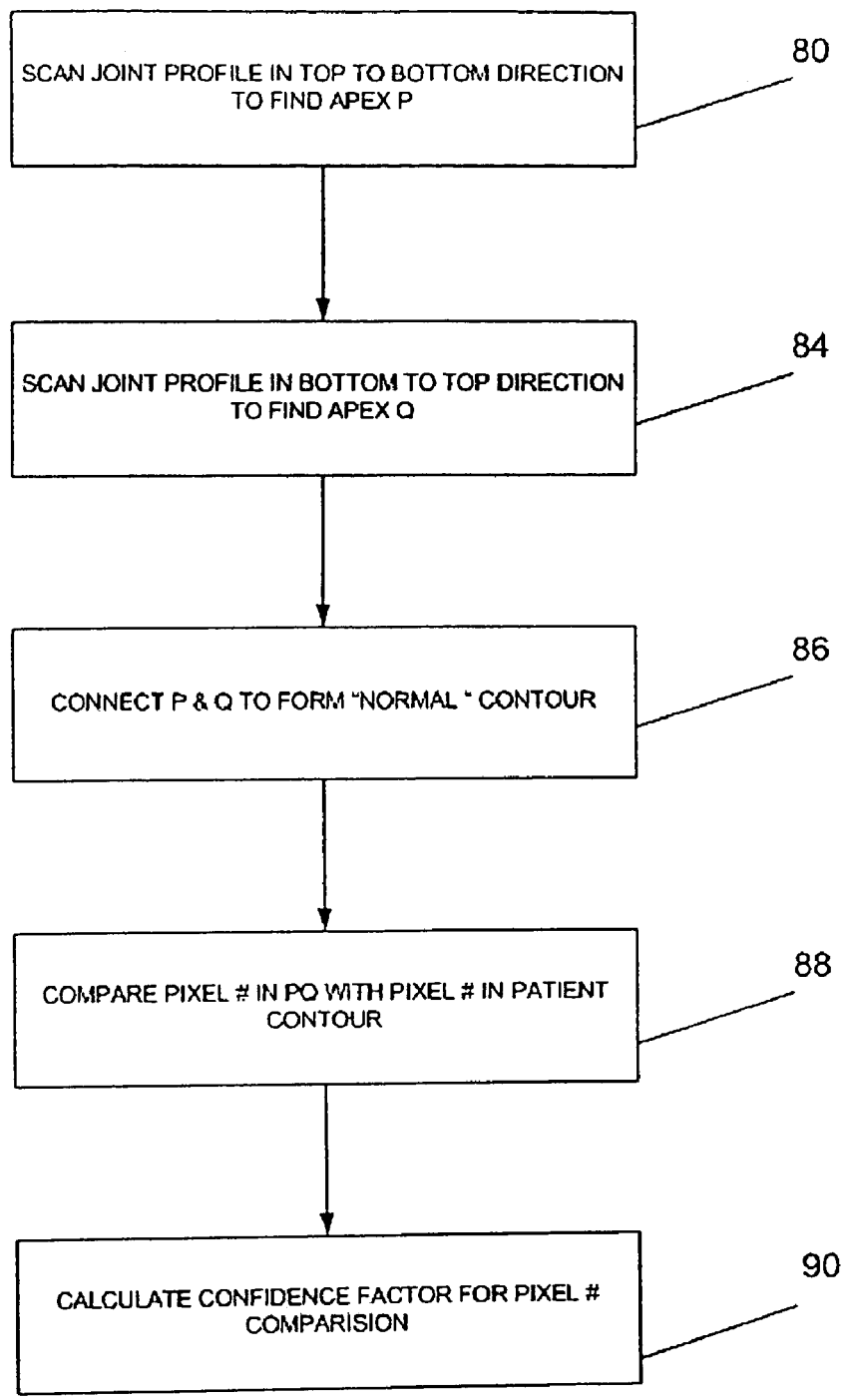
FIG. 5 is a flow diagram of steps in carrying out Embodiment 2 of the invention.

Once points P and Q are found, the program constructs a straight line 83 between the points, as indicated by box 86 in FIG. 5. This line represents a "normal" bone contour in this region (As indicated above, a normal bone may be slightly convex in this region). The points making up the patient bone contour segment between points P and Q can then be compared to the number of pixels making up the strait line connecting points P and Q (red trace in FIG. 4), to analyze the deviation between the straight line and the patient contour between the same two points. One measure of this deviation is the number of pixels contained in the each contour between points P and Q, the straight line contour represented the smallest pixel number between the two points, and the number of pixels in the patient contour being related to the extent of concavity in the contour. This operation is indicated at 88 in FIG. 5. The comparison of pixel numbers in the two contours can be expressed with criteria for a certainty or confidence factor (CF), as at 90 in FIG. 5. The system by default determines that the erosion exists if the CF exceeds a certain threshold, e.g., 60%, which can be determined by matching the automated algorithm to expert's assessment.

C. EMBODIMENT 3

Measuring Joint Bone Erosion

The method in this embodiment uses a portion of MP or PP templates to predict or estimate a normal contour (without erosion). Then, the current contour can be compared against the estimated contour to determine the existence and severity if the erosion.

From a MP or PP template, the algorithm defines two landmark points (described below in detailed steps) and applies a matching algorithm only on the contour points between them. By "copying over" the shape of the template's contour—the points between the two landmarks—for the area of interest (the area the erosion is supposed to occur), it is possible to partially overlay two contours and compare. The algorithm is shown in flow diagram in FIG. 7.

As a first step, indicated at box 92 in FIG. 7, the program finds the coordinates for an apical point P, as carried out in Embodiment 2, and the coordinates for the minimum width of the phalange (points N), as discussed below. These points are shown at P and N for a patient middle phalange 108 in FIG. 8A, and at $P_t$ and $N_t$, for a normal-bone template 110 in FIG. 8B.

$N=(x_n,y_n) \in B_c$, where $B_c$ is the current phalange contour $(x_a,y_n) \in B_c, (x_b,y_n) \in B_c$, $\min(|x_a-x_b|)$ in all $x_i$, where $1 \leq i \leq N$, N is the number of contour points That is, the program examines, for each y coordinate along the length of the bone, a coordinate for which the absolute value of $x_a-x_b$ on opposite sides of the bone that has a minimum value. The pair of x,y coordinates so identified are designated N. A similar algorithm finds the y coordinates adjacent at least bone end for which the absolute value $x_a-x_b$ is a maximum, and designates the corresponding x,y values as points P. These algorithms are also applied in Embodiments 1 and 4 for finding minimum-width coordinates and maximum-width apical coordinates.

In the operation of the program and with reference again to FIG. 7, a template is selected at 94 from a library of templates 96, constructed as described with respect to Embodiment 1. In determining whether the template is a good match for the patient contour, the program first calculates at 98 a scaling factor SF coordinates N, $N_t$, P, and $P_t$ determined for the patient and template contours as above. The scaling factor is calculated as the as the ratio of distances between P and N vs $P_t$ and $N_t$.

Figure 7:
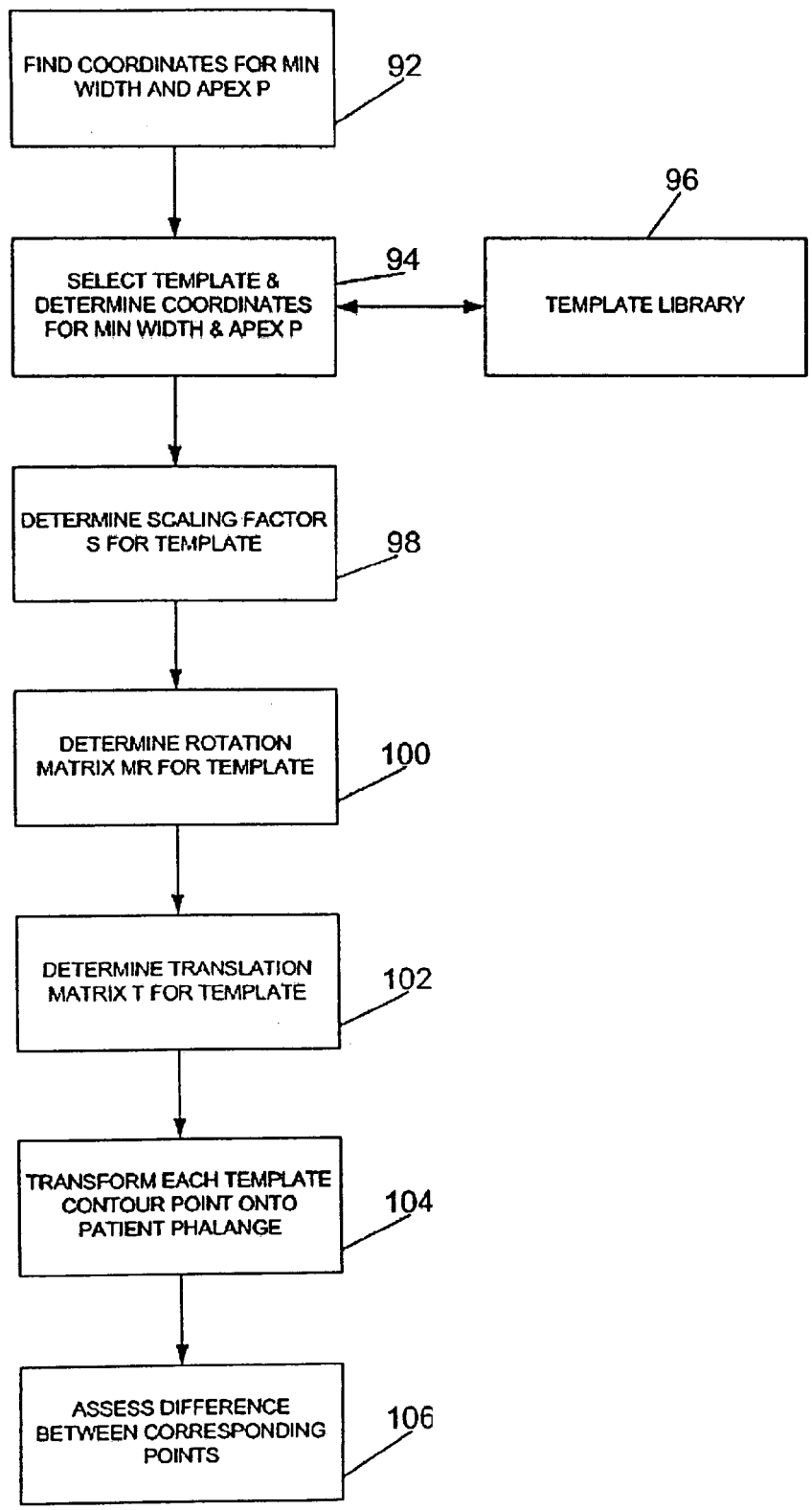
FIG. 7 is a flow diagram of steps in carrying out Embodiment 3 of the invention.
Figure 9A:
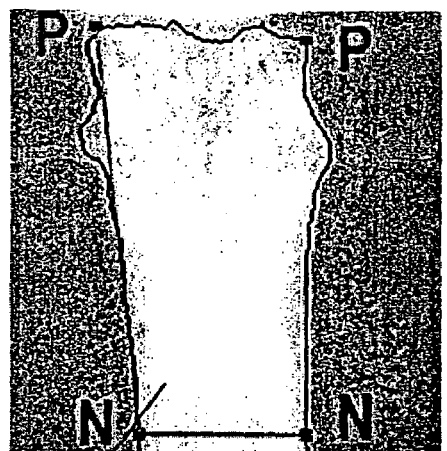
FIGS. 9A and 9B show lines connecting minimum width (N) and apical points (P) in a patient phalange joint region (9A) and corresponding template joint region (9B), for purposes of determining a scaling factor between the two contours.
Figure 9B:
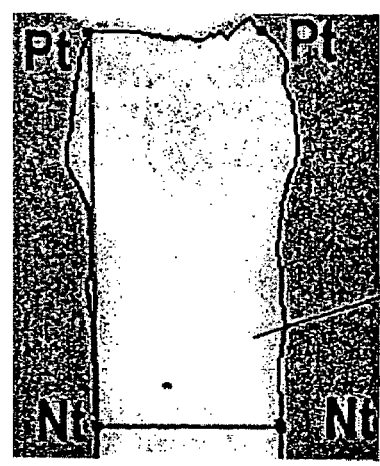

In addition to a scaling factor, the program calculates a rotation matrix for orienting the template and patient contours in the same plane, as indicated by box 100 in FIG. 7. This is done, as illustrated in FIGS. 9A and 9B, by forming lines P-N and N-N in the patient contour and corresponding lines $P_t$-$N_t$ and $N_t$-$N_t$ in the template contour. The rotation matrix is then determined by calculating the rotation angle, θ, as the angle between the line connecting P and N and $P_t$ and $N_t$ respectively. That is θ is the difference between the angle N-N-P in the patient contour and $N_t$-$N_t$-$P_t$ in the template contour. The rotation matrix is:

$$R = \begin{bmatrix} \cos\theta & \sin\theta \\ -\sin\theta & \cos\theta \end{bmatrix}$$

Figure 10A:
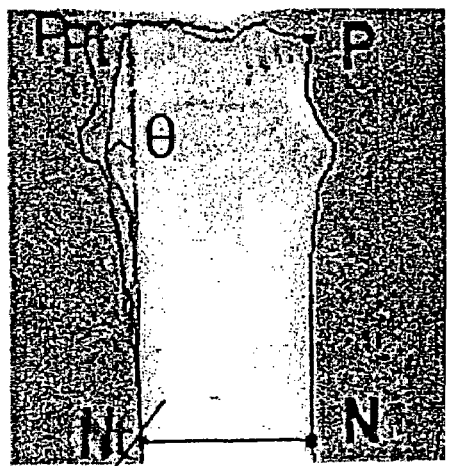
FIGS. 10A and 10B show the superposition of a scaled template phalange on a patient phalange before (10A) and after (10B) application of a rotation matrix.
Figure 10B:
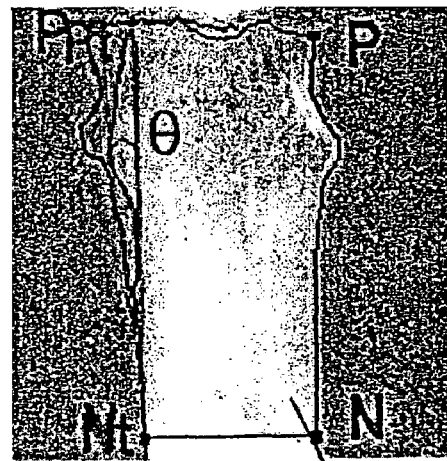

FIGS. 10A and 10B show the superimposition of the template contour on the patient contour before and after application of the rotation matrix.

The program now determines, at 102, a translation vector T for transforming each point between $P_t$ and $P_t$ of the template contour into the corresponding contour region between P and P in the patient contour.

Figure 11:
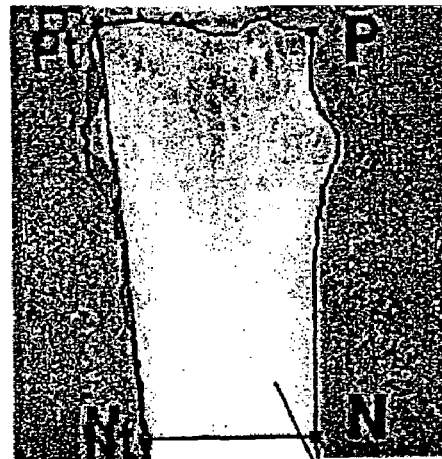
FIG. 11 shows erosion assessment after partial template overlay, in accordance with the method of Embodiment 3.

The final matrix transform M for superimposing the template contour on the patient contour is now calculated as:

$$M = sM_R + T,$$

where s is a scaling factor, R is a rotation matrix and T is a translation vector defined in the above steps. FIG. 11 shows the superposition of a template contour on a patient contour employing the matrix. As seen, the matrix has the effect of superimposing the template points $N_t$ and $P_t$ on the corresponding patient contour point N and P, respectively, for templates that have a good fit with the patient contour.

The above template matching is repeated for one or more templates in the library until a template that gives a best-fir superposition of the corresponding points N, P and $N_t$, $P_t$ between patient and template contours is found, as indicated at box 104 in FIG. 7.

After selection of a best-fit template, the extent of erosion of the patient bone is analyzed, as at 106, by comparing the template line contour in the joint region with the actual patient contour in the same region, to determine the extent to which the actual patient contour deviates from the normal-phalange contour. In particular, the program analyzes the differences in contours between N and P on the left side of the bone, P and P across the top of the bone, and P and P on the right side of the bone. In the N-P analysis, the algorithm scans in the y direction, recording for each y coordinate, the difference between the patient and contour x coordinate positions. Across the top of the bone, the scan is in the x direction, the difference value is for the contour y coordinates. When the scan is complete, an erosion value is determined, e.g., the average value of "negative" contour differences, that is, contour differences in which the template value is greater than the patient contour value.

The above method may be employed with either partial or total template. This method employs basically the same technique as described below for Embodiment 4, except that due to shape and size variances between the template and the real phalange contour, a number of small non-matched regions might exist. The subsequent necessary step is to analyze each of those regions and determine if it is generated by the minor variances or actual erosion. The criteria used is based on a shape analysis algorithm: long and thin regions are most likely generated by the minor variances, while jogged areas are erosions.

D. EMBODIMENT 4

Measuring Joint Bone Erosion

Figure 13:
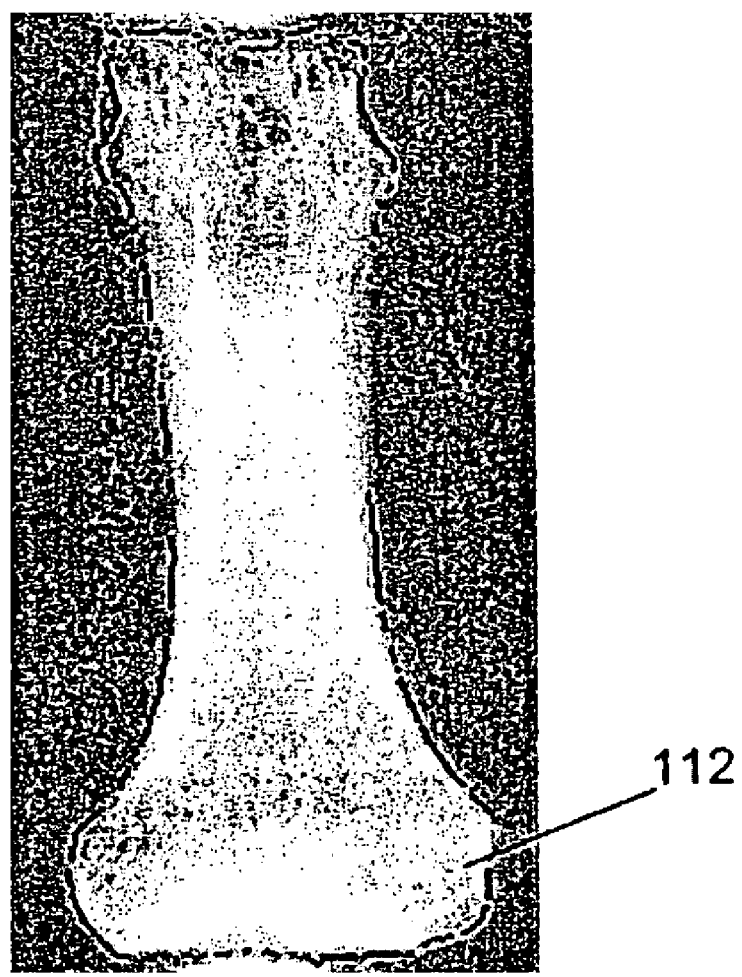
FIG. 13 illustrates patient reference and patient-bone contours in the distal joint region of the PP, for assessing bone erosion by the method of Embodiment 4.

If A patient has the bone contour obtained and stored in the previous visit or analysis, it is possible to accurately monitor the progression of erosion by using it as a template. The contour of the previous analysis is retrieved from the database and used as a shape template by overlaying it on the current contour, as shown at 112 in FIG. 13. The black contour represents the result of the current analysis, and the yellow one obtained in the previous analysis, respectively. The orange area indicates increased erosion development whereas the green area on the right shows improvement in erosion.

Figure 12:
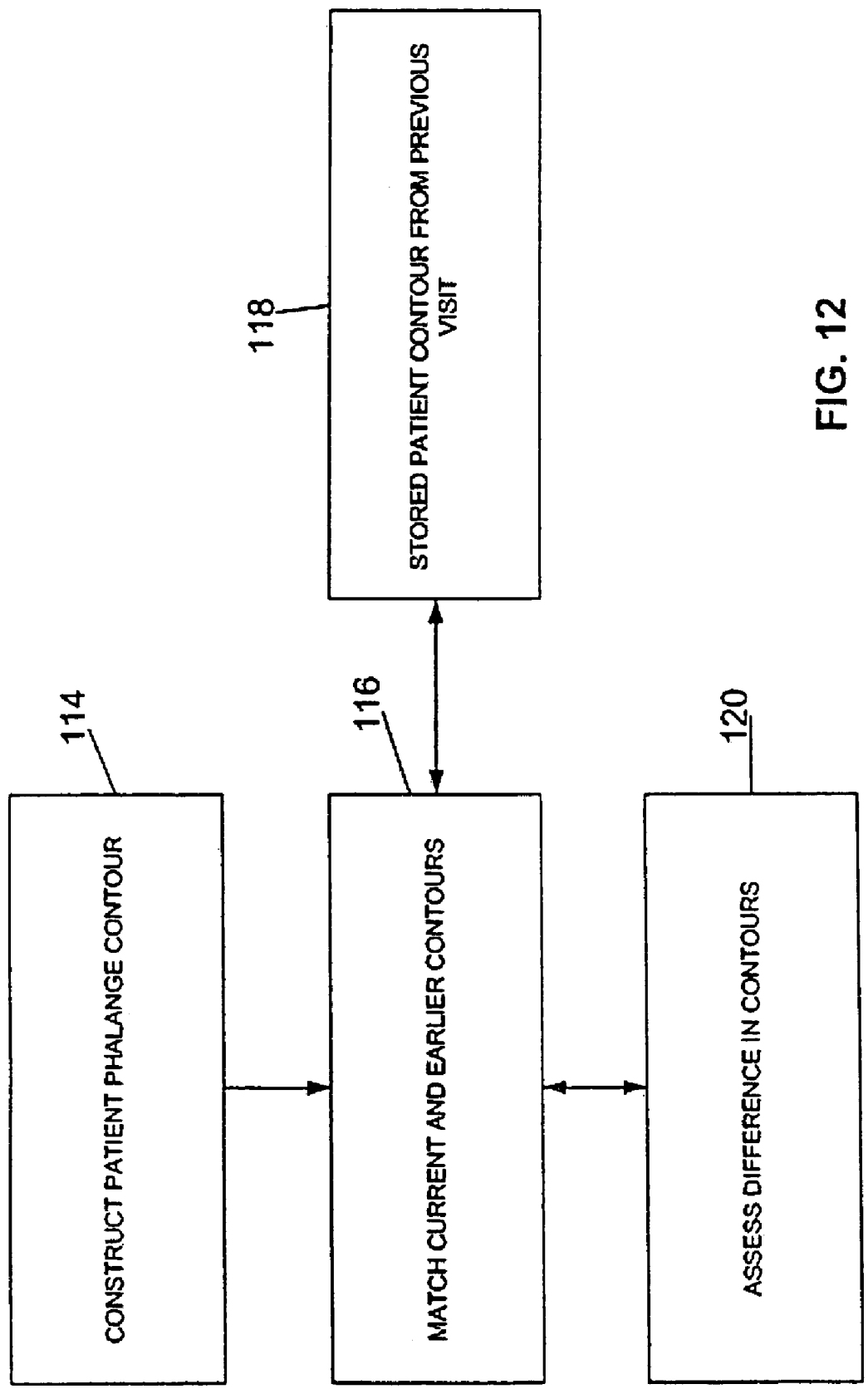
FIG. 12 is a flow diagram of steps in carrying out Embodiment 4 of the invention.

The operation of the algorithm in this method is shown in FIG. 12. Initially, the program constructs the current patient contour (box 114), according to previously discussed methods. This contour is then matched at 116 with one or more earlier patient-phalange contours stored at 118. The operation of the algorithm for matching the current ($B_c$) and previous ($B_p$) bone contours, and for assessing the differences between the two are as follows:

Given that the x-ray will be re-taken according to consistent AP guidelines, it is reasonable to expect that the contours in comparison should be almost identical in shape except for the areas of erosion. Therefore, it is possible to perform an accurate overlay of the template on the current bone contour, employing a scaling factor (SF) and anchoring points.

The scaling factor indicates how much the template should be expanded or shrunk. This is simply calculated by comparing lengths of bones in the two contours. Since these two contours are from the same patient, they are expected to yield a value close to 1.

$$SF = \frac{\max(y) \in B_c - \min(y) \in B_c}{\max(y) \in B_p - \min(y) \in B_p}$$

The anchoring points determine whether a translation and/or rotation are needed. They are used to align the shape template with the current contour. In this case, axes of each contour are aligned to achieve the overlay. Suppose there is a point that belonged to the previous contour, $(x,y) \in B_p$, and there is a corresponding point $(x',y')$ belongs to the current contour, $(x', y') = SF*(x-\Delta_x, y-\Delta_y)$ where $\Delta_x = x_c - x_p$, $(x_p, y) \in B_p$, and $(x_c, y) \in B_c$ $\Delta_y = \min(y) \in B_c - \min(y) \in B_p$ Since the angles of axes are expected to be almost identical, very little translation and/or rotation of the template, if any, will be needed.

Once the two contours are superimposed (box 116 in FIG. 12) the program determines an overlay function which is used in assessing the differences in the areas of the two contours (box 120 in FIG. 12). The overlay function has the form:

$O(B_c, B_p) = A_i$ where $A_i$ represents an area created from the contour overlay difference, where $0 \leq i \leq n$, n is the total number of areas. Assuming there is a point inside the area Ai, which is $(x_i, y_i) \in A_i$ and $y_m \leq y_i \leq y_q$ where $y_m$ and $y_q$ are similarly defined as in the concave test in the previous section. Erosion treatment improvement is then defined as (for left side)

$$I(B_c, B_p) = \begin{cases} \text{true} & \text{if all}(x_i, y_i) \in B_c \text{ and } x_i \leq x_j, (x_j, y_j) \in B_p \\ \text{false} & \text{otherwise} \end{cases}$$

Once $B_c$ and $B_p$ are overlaid, the numbers of points in $B_c$ that are inside (closer to the axis) of $B_p$ are counted.

The confidence factor can be represented as (from area Ai)

$$cf = \frac{n((x_c, y') \in B_c)}{\max(y) \in A_i - \min(y) \in A_i + 1}$$

such that $x_c < x_p$, $(x_p, y') \in B_p$, $n((x,y))$ is a function that returns the number of points.

These points indicate erosion has occurred.

E. Correction for Severely Curved Fingers

The method described above assume that fingers are almost straight or only slightly curved. If the finger to analyze is severely curved, as it can be in joint degenerative or joint-damaging disease, the analysis may initial require a correction to place the bones, e.g., phalanges forming the joint being analyzed along the same long axis.

The correction method described below is based on the observation that an axis of a finger is composed of a straight line axis of a distal phalange, that of a middle phalange and that of a proximal phalange. Therefore, even if the overall axis of a finger may be severely curved, its axis can be obtained by composing each of the three straight line axes for the three bones inside a finger.

Figure 14:
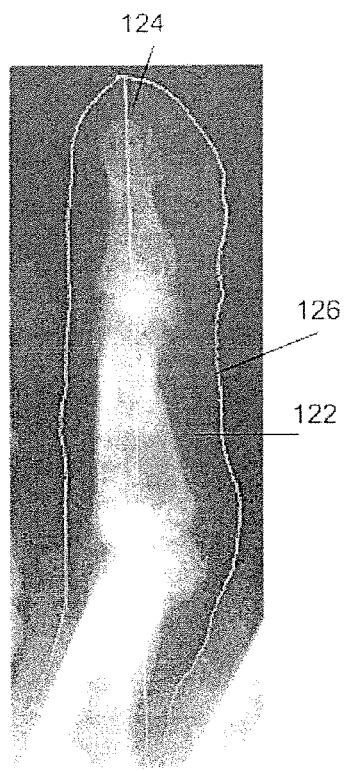
Figure 14:
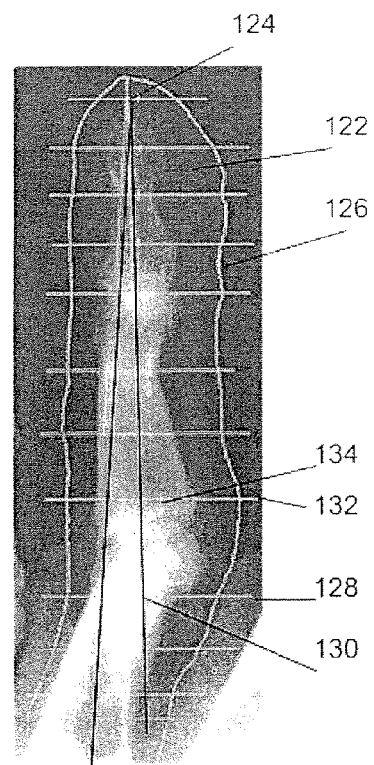
Figure 14:
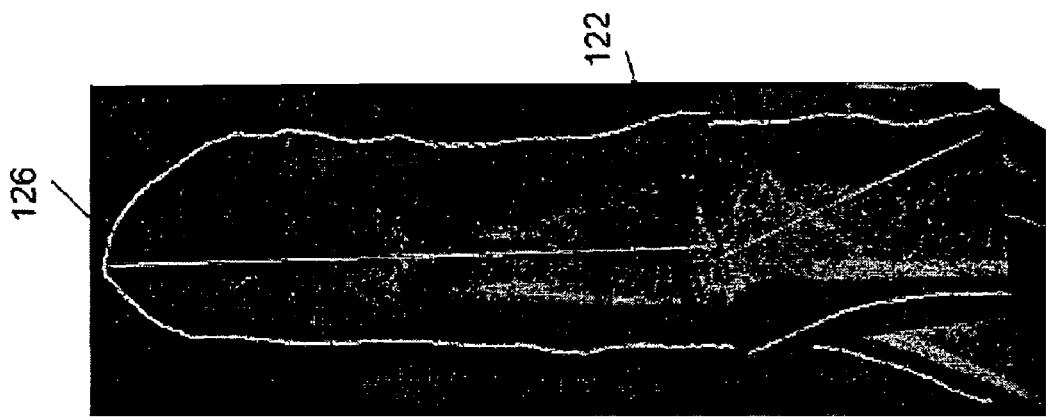
Figure 14:
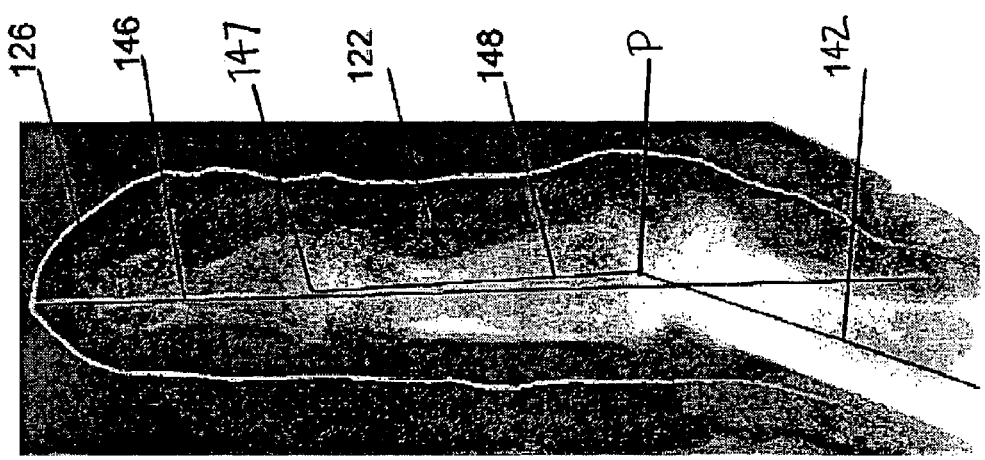
Figure 14:
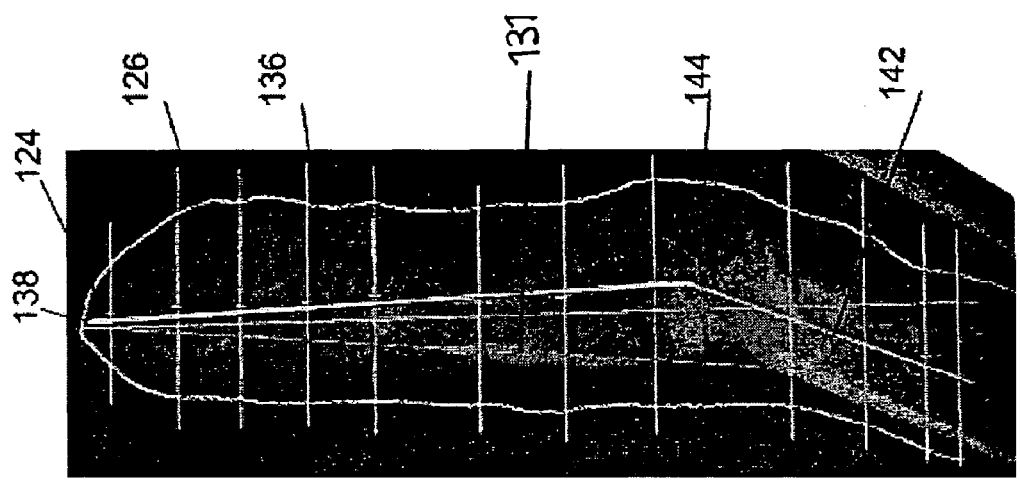

Each step can be elaborated as follows. First, obtain a contour of a finger, and obtain an approximate straight line axis of a finger using any conventional method, as indicated in FIG. 14A, which shows a severely curved finger 122, a straight-line axis 124 determined from the distal and middle phalanges, and the outer contour of the finger at 126. One algorithm calculates a central axis of the finger based on the center of gravity of the finger as determined from the outer contour. The entire finger is then rotated to an upright position along this axis, as indicated in FIG. 14A, that is, the center axis is oriented to a vertical line.

Next, the program scans the finger along the length of the axis (the y axis) to determine a midpoint along each scan line (x-axis direction). These steps are illustrated in FIG. 14B, which shows midpoints 130, 134 for scan lines 128, 132, respectively. The program now connects the first and last midpoints, to give line 131.

With reference to FIG. 14C. the program now calculates the distance between line 131 and each midpoint. The point on the scan line having the maximum distance from line 131 is determined, referred to herein as $P_1$, and is identified at 144 in FIG. 14C. As seen, point $P_1$ is close to the MP/PP joint in this figure. Next, the program constructs a line 136 from the highest midpoint to point $P_1$, and a second line 142 from point $P_1$ to the lowest scan line midpoint.

This same procedure is repeated to find a second point $P_2$ used in generating another phalange axis. This is done by determining the maximum distance of each scan midpoint from line 136 or from line 142. The greater of these maxima will define point $P_2$ at the midpoint on a scan line intersected by one of the two lines 136 or 142. In the present case, P2 is identified at point 147, corresponding roughly to the joint between the middle and distal phalanges, as seen in FIG. 14D. Line 136 is now divided into two lines, a line 146 between the dital tip and point P2, and a line 148 between points p1, and P2.

Each finger phalange is now rotated, as shown in FIG. 14E, to bring the line segment assigned to it into line with center axis 124. The program then operates to connect the three rotated phalanges from top to bottom to obtain artificially composed straight finger contour. This "straightened" contour is then is for further analysis in the method above.

The invention thus includes a method for orienting a severely curved finger into a straightened condition, for purposes of establishing a more normal orientation of the finger preliminary to the method steps above, where the bone contour is matched with template of previous-patient contours. The method includes constructing horizontal scan lines along the length of the finger, and determining midpoints of these scan lines. These midpoints are then used find points of maximum deviation of a line connecting the end midpoints with the midpoints themselves, as a basis for dividing the connecting line into two lines intersecting at this point of maximum deviation. Once the one or more points of maximum deviation are found, the separate portions of the finger may be rotated to bring each connecting line into conformity with a common vertical axis.

F. Periarticular Osteoporosis Measurement

Applying the existing OsteoGram technology to the scan box region, BMD adjacent to the joint space (or inside the scan box described above) is calculated pixel-by-pixel (U.S. Pat. No. 6,246,745). This BMD is a local bone loss value that is different from the comprehensive phalange BMD reported from the patent 745. It only evaluates the BMD adjacent to the joint area so that it will reflect the progression of the joint degeneration more precisely. In addition, this local BMD can be further separated to trabecular(axial) and cortical (peripheral) BMD, while the combined cortical thickness near the joint is considered as a better indicator for early RA disease.

Two possible algorithms can be used to automatically distinguish the two bone tissues:

Threshold algorithm: A local histogram profile is created for the region inside the scan box shown in FIG. 4. A cortical threshold is defined and a binary image will be created based on this threshold. A bug-following algorithm from pending patent Ser. No. 09/430,054 is then used to extract the cortical area.

Region growing algorithm. This algorithm starts with a set of cortical seed points that selected immediately from the phalange confront ends to grow regions by appending to each seed point those neighboring pixels that have similar gray levels.

An overall radiological score for monitoring the progression of the bone deformity disease will be reported after an X-ray radiograph is analyzed using the above method. The score will include the information of JSW, bone erosion and periarticular BMD status.

From the foregoing, it will be appreciated how various objects and features of the invention are met. The method allows for accurate quantitative determination and monitoring of both joint deformity and bone erosion, using only standard patient x-ray images for analysis. The method, as embodied in the code and system of the invention, is carried out in a nearly fully automated manner, allowing rapid and relatively assessment of joint and bone degeneration.

Although the application has been described with respect to certain embodiments and applications, it will be appreciated how various changes and modifications may be made without departing from the invention as claimed.

It is claimed:

1. An automated method of assaying or monitoring the extent of joint or bone deformity in a joint-degenerative or joint-damaging disease in a subject, comprising the steps of
   (a) determining from a digitized x-ray image of a patient's selected straight bone that terminates at a joint, coordinates of at least one of the right and left bone contours of a selected bone,
   (b) determining from bone contour coordinates determined in step (a), the coordinates of one or more apices in a region adjacent at least one side of the joint formed by the selected bone, and, optionally, the coordinates of a minimum width in the middle region of the bone,
   (c) using the coordinates determined in step (b) for selecting a reference joint contour corresponding to one of (i) the contours of confronting joint portions of adjacent straight bones in a normal joint formed by the selected bone; (ii) the contour of a normal joint in a joint region formed by the selected bone; and (iii) the contour from previous x-ray of the subject's bone in the region of the joint, and
   (d) guided by the reference joint contour selected in step (c), analyzing a region of the selected joint of the patient, to assay or monitor the extent of bone or joint deformity in the subject.

2. The method of claim 1, wherein the selected bone is a finger phalange terminating in a finger joint, or a toe phalange terminating in a toe joint.

3. The method of claim 2, wherein step (c) includes matching contour coordinates for a selected patient phalange determined from step (b) with one or more of a plurality of normal-phalange templates from a library of templates.

4. The method of claim 3, wherein each normal-phalange template in a library has been generated, for given patient characteristic(s) related to one or more of gender, age, ethnic group, hand size and body size, as a statistical average of a plurality of normal-phalange templates for the given patient characteristic(s).

5. The method of claim 2, wherein the selected bone is the middle or proximal phalange of a patient's finger.

6. The method of claim 5, for use in assaying or monitoring joint space width in a patient joint, wherein
   step (c) includes (ci) matching the coordinates of a minimum width in the middle region of the phalange and one or more apices on at least one side of the selected phalange adjacent said joint with corresponding coordinates in a normal-finger template, to identify a normal-finger template that matches the subject phalange, (cii) superimposing the normal-finger template phalange on the image of the patient-finger phalange, and (ciii) using the contours of the template finger to identify a scanning box at one of the joints of the selected phalange, and
   step (d) includes (di) scanning one of the joints of the selected phalange within said scanning box, in scanning directions substantially parallel to the axis of the finger, to generate contours of the confronting ends of the phalanges in said joint, (dii) generating profiles of the distances between said confronting phalange bone-end contours within said scan box, and (diii) analyzing said profiles from (ii) to determine the extent of bone loss at said joint, as an indicator of extent or progression of joint-damaging disease in said subject.

7. The method of claim 6, wherein the selected phalange is the middle phalange, and the scanning box is placed at the middle phalange/proximal phalange (MP/PP) joint.

8. The method of claim 7, wherein step (ci) includes using the coordinates of the minimum middle phalange width to determine a scaling factor for superimposing the template finger of the image of the patient finger.

9. The method of claim 7, wherein step (ci) further includes matching the determined coordinates of a patient-finger middle flange with the corresponding coordinates of the middle phalange of each of a set of template fingers, assessing the difference between the two, and based on this difference, either accepting the template or matching another template from the set.

10. The method of claim 7, wherein step (ciii) includes finding a first line extending through the widest portion of the middle phalange in the region of the MP/PP joint, finding a second line parallel to the first which extends through the widest portion of the adjacent phalange in the region of the same joint, and connecting the two lines with parallel connecting lines to form a rectangular scanning box defined by said widest bone portions.

11. The method of claim 5, wherein step (d) includes successively scanning across said joint, in a direction substantially parallel to the finger axis, and the scan line an incremental distance along the width of the scan box, until scans along the entire width of the box have been taken.

12. The method of claim 11 wherein the selected phalange is the middle phalange, and the scanning box is placed at the middle phalange/proximal phalange (MP/PP) joint, and step (dii) includes comparing the distances at each point along the scan box in said profile with those representative of a normal-subject MP/PP joint from the same finger as the patient finger.

13. The method of claim 5, for use in assaying or monitoring bone erosion in a patient joint, wherein
   step (c) includes (ci) from the determined coordinates of the contours of the selected phalange, identifying a pair of apices on at least one side of the selected phalange adjacent said joint, and (cii) constructing a straight line between each the apices in each pair, where said straight line represents a reference joint contour adjacent the joint region of the selected phalange, and step (d) includes comparing the straight line contour between a pair of apices with the actual patient contour between the same two points, to determine the extent of concavity of said region with respect to the straight line extending between the two apices.

14. The method of claim 13, wherein the selected phalange is the proximal phalange, and the joint is the MP/PP joint.

15. The method of claim 5, for use in assaying or monitoring bone erosion in a patient joint, wherein step (c) includes (ci) matching the coordinates of a minimum width coordinate in the middle region of the phalange and one or more apices on at least one side of the selected phalange adjacent said joint with corresponding coordinates in a partial or complete normal-finger template, to identify a joint region of a normal-finger phalange template that matches the subject finger joint region, and (cii) superimposing the contour of the template phalange joint region on the image of the patient-finger phalange joint region, where the template contour represents a reference joint contour adjacent the joint region of the selected phalange, and step (d) includes comparing the template line contour in the joint region with the actual patient contour in the same region, to determine the extent to which the actual patient contour deviates from the normal-phalange contour.

16. The method of claim 15, wherein the selected phalange is the proximal phalange, and the joint is the MP/PP joint.

17. The method of claim 5, for use in assaying or monitoring bone erosion in a patient joint, wherein step (c) include (ci) matching the coordinates of a minimum width coordinate in the middle region of the phalange and one or more apices on at least one side of the selected phalange adjacent said joint with corresponding coordinates in a previous patient x-ray image of the finger phalange, and (cii) superimposing the contour of the previous x-ray image phalange joint region on the image of the patient-finger phalange joint region, where the previous-patient contour represents a reference joint contour adjacent the joint region of the selected phalange, and step (d) includes comparing the previous-image contour in the joint region with the actual patient contour in the same region, to determine the extent to which the actual patient contour deviates from the previous-image contour.

18. The method of claim 17, wherein the selected phalange is the proximal phalange, and the joint is the MP/PP joint.

19. An automated system for use in assaying or monitoring the extent of joint or bone deformity in a joint-degenerative or joint-damaging disease in a subject, comprising (A) an electronic computer, and (B) machine readable storage medium embodying computer-readable code which is operable, when used to control the operation of the computer, to carry out the steps in the method of claim 1, where the selecting step in the claimed method includes matching contour coordinates for a selected patient phalange determined from step (b) with each of a plurality of normal-phalange templates from a library of templates, and (C) a library of normal-phalange templates which is accessible by said code for use in carrying out step (c) in the method.

20. A machine readable storage medium embodying computer-readable code which is operable, when used to control the operation of an electronic computer, to assay or monitor the extent of joint or bone deformity in a joint-degenerative or joint-damaging disease in a subject, by the steps of (a) determining from a digitized x-ray image of a patient's selected straight bone that terminates at a joint, coordinates of at least one of the right and left bone contours of a selected bone, (b) determining from bone contour coordinates determined in step (a), the coordinates of one or more apices in a region adjacent at least one side of the joint formed by the selected bone, and, optionally, the coordinates of a minimum width in the middle region of the bone, (c) using the coordinates determined in step (b) for selecting a reference joint contour corresponding to one of (i) the contours of confronting joint portions of adjacent straight bones in a normal joint formed by the selected bone; (ii) the contour of a normal joint in a region adjacent at least one side of the joint formed by the selected bone, and (iii) the contour of the subject's joint in a region adjacent at least one side of the joint formed by the selected bone, and (d) guided by the reference joint contour selected in step (c), analyzing a region of the selected joint of the patient, to assay or monitor the extent of joint or bone deformity in the subject.

21. The storage medium of claim 20, wherein the selected bone is a finger phalange defining a finger joint, or a toe phalange defining a toe joint.

22. The storage medium of claim 21, wherein the selected bone is a middle or proximal phalange of a patient's finger.

23. The storage medium of claim 22, for use in assaying or monitoring joint space width in a patient joint, wherein step (c) includes (ci) matching the coordinates of a minimum width in the middle region of the phalange and one or more apices on at least one side of the selected phalange adjacent said joint with corresponding coordinates in a normal-finger template, to identify a normal-finger template that matches the subject phalange, (cii) superimposing the normal-finger template phalange on the image of the patient-finger phalange, and (ciii) using the contours of the template finger to identify a scanning box at one of the joints of the selected phalange, and step (d) includes (di) scanning one of the joints of the selected phalange within said scanning box, in scanning directions substantially parallel to the axis of the finger, to generate contours of the confronting ends of the phalanges in said joint, (dii) generating profiles of the distances between said confronting phalange bone-end contours within said scan box, and (diii) analyzing said profiles (ii) to determine the extent of bone loss at said joint, as an indicator of extent or progression of joint-damaging disease in said subject.

24. The storage medium of claim 22, for use in assaying or monitoring bone erosion in a patient joint, wherein step (c) includes (ci) from the determined coordinates of the contours of the selected phalange, identifying a pair of apices on at least one side of the selected phalange adjacent said joint, and (cii) constructing a straight line between each the apices in each pair, where said straight line represents a reference joint contour adjacent the joint region of the selected phalange, and step (d) includes comparing the straight line contour between a pair of apices with the actual patient contour between the same two points, to determine the extent of concavity of said region with respect to the straight line extending between the two apices.

25. The storage medium of claim 22, for use in assaying or monitoring bone erosion in a patient joint, wherein step (c) includes (ci) matching the coordinates of a minimum width coordinate in the middle region of the phalange and one or more apices on at least one side of the selected phalange adjacent said joint with corresponding coordinates in a partial or complete normal-finger template, to identify a joint region of a normal-finger phalange template that matches the subject finger joint region, and (cii) superimposing the contour of the template phalange joint region on the image of the patient-finger phalange joint region, where the template contour represents a reference joint contour adjacent the joint region of the selected phalange, and step (d) includes comparing the template line contour in the joint region with the actual patient contour in the same region, to determine the extent to which the actual patient contour deviates from the normal-phalange contour.

26. The storage medium of claim 22, for use in assaying or monitoring bone erosion in a patient joint, wherein step (c) include (ci) matching the coordinates of a minimum width coordinate in the middle region of the phalange and one or more apices on at least one side of the selected phalange adjacent said joint with corresponding coordinates in a previous patient x-ray image of the finger phalange, and (cii) superimposing the contour of the previous x-ray image phalange joint region on the image of the patient-finger phalange joint region, where the previous-patient contour represents a reference joint contour adjacent the joint region of the selected phalange, and step (d) includes comparing the previous-image contour in the joint region with the actual patient contour in the same region, to determine the extent to which the actual patient contour deviates from the previous-image contour.

27. The system of claim 26, wherein each normal-phalange template in a library has been generated, for given patient characteristic(s) related to one or more of gender, age, ethnic group, hand size and body size, as a statistical average of a plurality of normal-phalange templates for the given patient characteristic(s).

* * * * *